United States Patent [19]

Hakala et al.

[11] Patent Number: 4,888,825

[45] Date of Patent: Dec. 26, 1989

[54] FULL VIEW WELDING SHIELD

[75] Inventors: Timo Hakala, Valkkinen; Reijo Lehtonen, Sääksjärvi, both of Finland

[73] Assignee: Euromaski OY, Forssa, Finland

[21] Appl. No.: 195,470

[22] Filed: May 13, 1988

Related U.S. Application Data

[63] Continuation of Ser. No. 787,797, filed as PCT FI85/00012 on Feb. 7, 1985, published as WO85/03429 on Aug. 15, 1985, abandoned.

[30] Foreign Application Priority Data

Feb. 10, 1984 [FI] Finland .................................. 840540

[51] Int. Cl.⁴ .............................................. A61F 9/06
[52] U.S. Cl. ................................................... 2/8; 2/9; 2/205
[58] Field of Search ..................... 2/8, 205, 432, 7, 9, 2/424, 410, 10, 5, 6; 128/201.12

[56] References Cited

U.S. PATENT DOCUMENTS

| | | | |
|---|---|---|---|
| 2,406,092 | 8/1946 | Meyer | 2/8 |
| 2,544,457 | 3/1951 | Harrington | 2/8 |
| 2,798,222 | 7/1957 | Evans et al. | 2/9 |
| 3,013,273 | 12/1961 | Kamperin | 2/5 |
| 3,112,490 | 12/1963 | Malcom, Jr. | 2/8 |
| 3,129,431 | 4/1964 | Haney | 2/8 |
| 3,189,918 | 6/1965 | Hiatt et al. | 2/9 |
| 3,380,073 | 4/1968 | McLaughlin | 2/8 |
| 3,747,599 | 7/1973 | Malmin | 128/201.12 |
| 4,172,294 | 10/1979 | Harris | 2/8 X |

FOREIGN PATENT DOCUMENTS 2040118  8/1980  United Kingdom .................. 2/8

*Primary Examiner*—Peter Nerbun
*Attorney, Agent, or Firm*—Ladas & Parry

[57] ABSTRACT

The invention relates to a protecting device, especially a welding shield. The protecting device consists of a portion protecting from radiation and sparks, which portion is arranged to rest on the head and at the eyes provide with a protecting glass (3) turnable upwards. To provide a wide field of vision and an intensive protection, the portion (1) protecting from radiation and sparks is manufactured of a transparent material to a continuous portion without openings. Moreover, a visor (2) is turnably journalled to the projecting portion (1), at least a part of which visor is arranged to form the protecting glass (3). The protecting portion (1) can be formed to a helmet-shaped portion protecting the head from all sides.

19 Claims, 1 Drawing Sheet

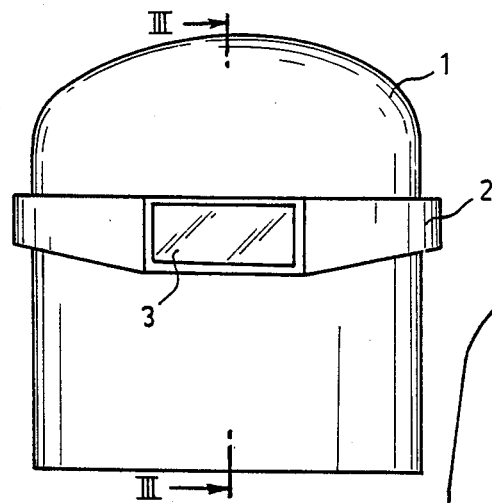
FIG. 1
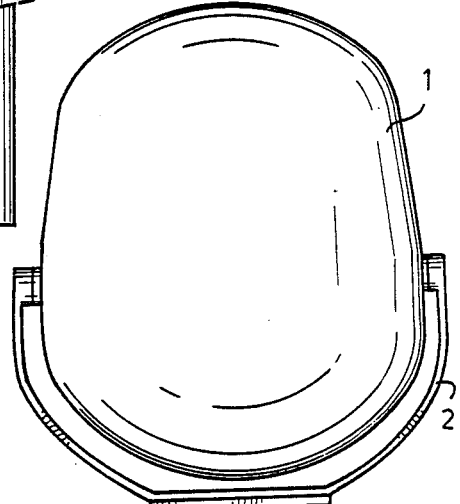
FIG. 2
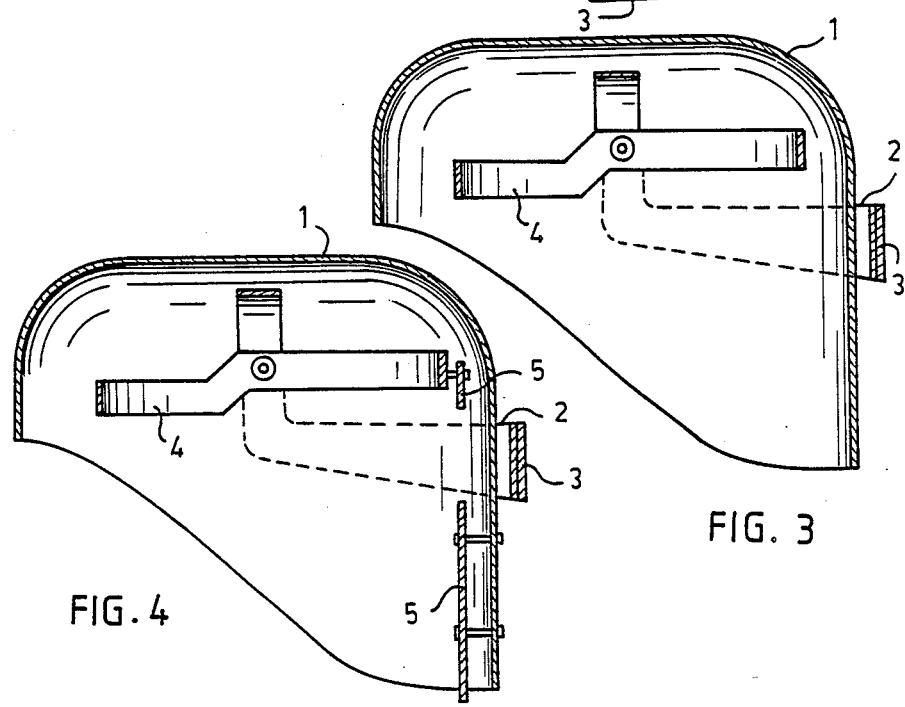
FIG. 3
FIG. 4

FULL VIEW WELDING SHIELD

This is a continuation of Ser. No. 787,797, filed as PCT FI85/00012 on Feb. 7, 1985, published as WO85/03429 on Aug. 15, 1985, now abandoned.

The invention relates to a protecting device, especially a welding shield, consisting of a portion protecting from radiation and sparks, which portion is arranged to rest on the head and at the eyes provided with a protecting glass turnable upwards.

Such protecting devices are widely known, especially at welding. The most common construction consists of a helmet of a not-transparent material, e.g. wood, metal etc., which helmet is arranged to rest on the head so that it protects the face of the welder. Moreover, the helmet is often provided with hinges at its upper edge so that it can be lifted up when no shield is needed. The helmet is additionally provided with an opening at the eyes, in which opening is arranged a protecting glass which can be opened. In practice the welding point in question can be observed during welding through said protecting glass.

A corresponding construction has been used also as embodiments intended to be supported by hand during the whole welding procedure.

The simplest version of the known devices is a plain planar sheet provided with a grip, by means of which the welder can hold the sheet between the welding point and his eyes. This device is in the first place intended to be used by amateurs.

The common disadvantage of all the known protecting devices is that the field of vision of the welder is extremely limited, when the shield is in its place. Additionally, for turning the protecting glass or turning down the whole protecting device, a hand or some kind of a quick motion with the head is needed. Because of the limited field of vision, the welder cannot always see his surroundings, whereby risk situations rather easily appear. Turning the protecting glass takes time again and the whole step is difficult e.g. when the welder is wearing gloves. By turning the protecting glass, it is, however, only possible to provide an extremely restricted field of vision, whereby it is customary to lift off the whole protecting helmet from the face. The protecting helmet cannot, however, always be properly placed in the upper position because of lack of space, this disadvantage has been noticed especially at repair works. When turning down the protecting helmet or the protecting glass, the motions needed easily lead to that the welding rod is moving from the right point as a consequence of the motions mentioned. A disadvantage of all known protecting devices is also that they are suitable to be used as protecting devices at welding only and correspondingly, protecting devices intended to be used at other kinds of work are not suitable to be used at welding.

The intention of the invention is to produce a protecting device not having the disadvantages of the known protecting devices and still being advantageous to manufacture and comfortable to use.

This has been achieved by means of the protecting device of this invention, characterized in that the portion protecting from radiation and sparks is manufactured of a material at least limiting the passage of injurious radiation, but being transparent in the direction of the user's eyes, to form a continuous portion without an opening, and that a visor is turnably journalled to the protecting portion, at least a part of which visor is arranged to form a protecting glass.

The advantage of a device according to the invention is that this protecting device suits well to various works, because the field of vision is wide and the head always protected from each side. During welding, the welding rod can easily be directed to the right point before ignition and also be held there, because the rod can, if needed, be supported by both hands and because no sudden motions of a hand or the head are needed to turn the protecting device or a part thereof into a protecting position. The protecting device of the invention eliminates well also the disadvantages of the radiation coming into the eyes from the side without anyway substantially limiting the field of vision. The protecting device of the invention also protects well from heat. Moreover, the device of the invention is light and owing to its construction, balanced, which makes it comfortable to use. Additionally, the manufacturing costs are advantageous.

In the following, the invention will be described by means of preferable embodiments according to the drawings enclosed, whereby FIG. 1 is a frontal view of the protecting device of the invention, FIG. 2 shows the protecting device of FIG. 1 from above, FIG. 3 illustrates the invention as a section parallel with the line III—III of FIG. 1, FIG. 4 is a cross-section of the second embodiment of the invention.

In the example of the figures, the portion protecting from radiation and sparks, which portion is arranged to rest on the head, is marked by a reference 1. The visor turnably arranged in the protecting portion 1 is marked by a reference 2. The protecting glass again is marked by a reference 3. The means which are used for placing the protecting device to rest on the head is marked by a reference 4. The means 4 mentioned above are in principle presented in FIG. 3. Protecting sheets used in the second preferable embodiment of the invention (FIG. 4) are denoted by a reference 5.

The portion 1 protecting from radiation and sparks is according to the invention manufactured of a material preventing or at least reducing the passage of the radiation, but which material nevertheless is transparent in the opposite direction, i.e. seen away from the eyes of the welder. Due to the transparence of the material, it has been possible to make the portion 1 protecting from radiation and sparks to a continuous construction, consequently, without an opening at the eyes known from the prior art protecting devices.

Further, to the portion 1 protecting from radiation and sparks is turnably journalled a visor 2, at least a part of which is arranged to form a protecting glass 3 for observing the welding point during the very welding. The journalling points of the visor 2 are located on both sides of the protecting portion 1 and the visor 2 itself is arranged to extend around the front side of the protecting portion 1. The term "around the front side" means here that the visor 2 extends around the front side of the protecting portion 1 when the visor 2 is in its normal protecting position, which is shown in the figures. The visor 2 can be turned up, if needed, such position is preferable e.g. when not welding, but some other kind of work is done, e.g. grinding, fitting of welded bodies etc.

According to the invention, it has been found to be especially preferable to form the portion 1 protecting from radiation and sparks to a helmet-shaped portion protecting the head from all sides. Then the protecting means suit especially well for various kinds of work. Especially at repairings, when the working conditions often are very difficult, the space reserved for the work is limited and various tools must be used, a protecting device of this kind protecting the head from all sides and making the welding possible has been found very practical.

The portion 1 protecting from radiation and sparks can be manufactured of any material which does not transmit radiation to a disadvantageous extent and which prevents the passage of sparks, but still is transparent in the opposite direction. As manufacturing material can be used e.g. transparent plastic material, on the surface of which is arranged a film not letting radiation through but being transparent in the other direction. Such films are known per se from various window constructions, whereby the films in question also are called "sun absorbing films".

According to the invention, it is also possible to manufacture the portion 1 protecting from radiation and sparks of a transparent shaded plastic material preventing the injurious part of the radiation from passing through.

According to the invention, it is possible to locate the protecting glass 3 in the visor 2 so that only a part of the visor 2 forms the protecting glass 3. However, nothing prevents from manufacturing the whole visor 2 as a protecting glass, whereby the admission of welding radiation into the eyes from side directions is especially well prevented.

According to the invention, it is also possible to provide the portion 1 protecting from radiation and sparks with at least one protecting sheet 5 arranged inside the portion. A protecting sheet or sheets 5 are thereby arranged at a distance from the portion 1 protecting from radiation and sparks. Such an embodiment is shown in FIG. 4. The protecting sheet 5 can then be manufactured of the same material as the portion 1 protecting from radiation and sparks. Thus, as material can for instance be used shaded plastic or plastic provided with a film preventing the passage of the radiation. However, there is nothing to prevent that the protecting sheet 5 is manufactured of a non-transparent material or of the same material as the protecting glass 3.

The main characteristics of the working idea of the invention are as follows. The protecting device is placed to rest on the head by using means 4. When the welding is started, the visor 2 is in the protecting position shown in the figures. The welding rod can before ignition be directed in an extremely preferable way by turning the head a little so that the point to be welded is seen either above or below the visor 2. At the moment of ignition, the head is lifted or respectively lowered a little, whereby the eyes are directed through the protecting glass 3 to the point to be welded. The invention is advantageous, because the motions of the head needed are very small and they can be made slowly, whereby the location of the rod certainly remains correct. The location of the rod is further assured by the possibility to use both hands when locating the rod, for no hands are needed when using this protecting device. If some other kind of work will be done after the welding and no protecting glass 3 is needed, the visor 2 can easily be turned up, i.e. away from the field of vision.

The visor 2 can easily be formed so that it does not substantially stand above the portion 1 protecting from radiation and sparks, whereby the visor can be turned up even if the space is limited. By means of the protecting device of the invention, an intensive protection can be achieved and in addition to that, a field of vision which is as wide as possible even during welding. A wide field of vision is of great significance e.g. when preventing fires.

In the embodiment of FIG. 4, the function is mainly quite the same as described in connection with the embodiment of FIGS. 1-3. The idea of this embodiment is that the user of the protecting device is able to see widely around himself, even if the protecting sheets mentioned are manufactured of a non-transparent or in normal circumstances non-transparent material. This is possible, because the protecting sheet or sheets are located at a distance from the portion 1 protecting from radiation and sparks, whereby it is possible to see through the slit between the protecting sheet 5 and the portion 1 protecting from radiation and sparks. Hereby, the field of vision becomes extremely wide when compared to the field of vision possible to achieve with the prior art protecting devices. If the protection sheet or sheets 5 are manufactured of the same material as the portion 1 protecting from radiation and sparks, the function of the construction entirely corresponds to that described in connection with the example of FIGS. 1-3. If the protecting sheet 5 is manufactured of a transparent material, the sheet can be continuous also at the eyes, otherwise an opening must be made in the protecting sheet 5 or the sheet must be manufactured in two parts, for instance as shown in the embodiment of FIG. 4.

The embodiments described above are by no means meant to limit the invention, but the invention can be modified in various ways within the scope of the claims. Consequently, the protecting device or its parts need not have exactly the form presented in the figures. The journalling of the visor, the limitations of its motions and the supporting elements of the protecting device can naturally be carried out in many different ways. The protecting sheet or sheets 5 can naturally be fastened in place in any known manner, e.g. by means of bolts etc.

We claim:

1. A protecting device in the form of a welding shield comprising:
    (a) a protecting part for being positioned on a head of a user for protecting the head from radiation and sparks, said protecting part substantially restricting passage of injurious radiation towards the head and being substantially transparent to a view of the user looking through said protective part from an inside thereof, whereby said protective part provides a full-view face shield;
    (b) a visor being pivoted for movement about an outside surface of said protecting part, said visor having a first position substantially in front of the eyes of the user and a second position away from the eyes of the user, said visor having a protecting glass means for protecting the eyes of the user from a welding arc, whereby the user has a clear view of surroundings with said visor in said second position and with said visor in said first position by looking above or below said visor.

2. A protecting device according to claim 1 wherein the protecting part is formed as a helmet-shaped portion protecting the head of the user from all sides.

3. A protecting device according to claim 1 wherein the protective part is manufactured from a transparent plastic material having a film preventing the passage of radiation from at least one direction and being transparent in the direction of outward view of a wearer, said film being positioned on at least one surface of the protecting part.

4. A protecting device according to claim 1 wherein the protecting part is manufactured from a shaded plastic material.

5. A protecting device according to claim 1, wherein said entire protecting glass means is made of a protecting glass.

6. A protecting device according to claim 1, wherein, at least one protecting sheet is arranged within an interior of the protecting part at a distance from the inside surface of the protecting part.

7. A protecting device according to claim 6, wherein the protecting sheet is manufactured from the same material as the protecting portion.

8. A protecting device according to claim 6, wherein the protecting sheet is manufactured from a non-transparent material.

9. A protecting device according to claim 6, wherein the protecting sheet is manufactured from the same material as the protecting glass.

10. A full view welding shield comprising:
  (a) a face shield for being positioned on a head of a user for protecting the head from radiation and sparks, said face shield being substantially transparent to visible light at ordinary light levels and substantially restricting passage of injurious radiation towards the head, said transparent face shield protecting the face of the user and providing an unrestricted view of a surrounding area by the user;
  (b) a visor having a protecting means for protecting the eyes of the user from intense light produced by a welding arc and being pivotably mounted for movement about an outside surface of said face shield, said visor having a first position substantially in front of the eyes of the user and covering a portion of said face shield directly in front of the eyes of the user and a second position away from the eyes of the user, whereby the user has an unrestricted view of said surrounding area with said visor in said second position and with said visor in said first position by looking above or below said covered portion of said face shield.

11. A welding shield according to claim 10 wherein the face shield is attached to a helmet-shaped portion protecting the head of the user from all sides.

12. A welding shield according to claim 10 wherein the face shield is manufactured from a transparent plastic material having a film preventing the passage of radiation from at least one direction and being transparent in the direction of outward view of a wearer, said film being positioned on at least one surface of the face shield.

13. A welding shield according to claim 10 wherein the face shield is manufactured from a shaded plastic material.

14. A welding shield according to claim 10 wherein said entire protecting means is made of a protecting glass.

15. A welding shield according to claim 10 wherein at least one protecting sheet is arranged within an interior of the face shield at a distance from the inside surface of the face shield.

16. A welding shield according to claim 15 wherein the protecting sheet is manufactured from the same material as the face shield.

17. A welding shield according to claim 15 wherein the protecting sheet is manufactured from a non-transparent material.

18. A welding shield according to claim 15 wherein the protecting sheet is manufacture from the same material as the protecting glass.

19. A full view welding shield comprising:
  (a) shield for being positioned on a head of a user for protecting the head from radiation and sparks, said shield consisting essentially of a material which is substantially transparent to visible light at ordinary light levels and substantially restricts passage of injurious radiation towards the head, said transparent shield protecting the head of the user and providing an unrestricted view of a surrounding area by the user;
  (a) a visor having a protecting means for protecting the eyes of the user from intense light produced by a welding arc and being pivotally mounted for movement about an outside surface of said shield, said visor having a first position substantially in front of the eyes of the user and covering a portion of said shield directly in front of the eyes of the user and a second position away from the eyes of the user whereby the user has an unrestricted view of said surrounding area with said visor in said second position and with said visor in said first position by looking above or below said covered portion of said shield.

* * * * *